United States Patent [19]

Thomas et al.

[11] 4,307,289
[45] Dec. 22, 1981

[54] CONTACT LENS DISINFECTING UNIT

[75] Inventors: Michael D. Thomas; Francis E. Ryder, both of Arab, Ala.

[73] Assignee: Ryder International Corporation, Arab, Ala.

[21] Appl. No.: 14,074

[22] Filed: Feb. 22, 1979

[51] Int. Cl.³ .............................................. A61L 2/04
[52] U.S. Cl. ................... 219/521; 219/386; 219/401; 422/300; 422/307
[58] Field of Search .............................. 219/385–387, 219/432, 433, 436, 438, 521, 530, 541, 439; 422/292, 300; 206/0.8; D24/9

[56] References Cited

U.S. PATENT DOCUMENTS

| 2,408,751 | 10/1946 | Breiter | 219/386 |
|---|---|---|---|
| 2,691,717 | 10/1954 | Huck | 219/530 |
| 2,799,767 | 7/1957 | Bremer | 219/541 |
| 3,037,107 | 5/1962 | Clark | 219/439 |
| 3,301,060 | 1/1967 | Kenmotsu | 73/343 |
| 3,494,321 | 2/1970 | Moore et al. | 116/114.5 |
| 3,801,278 | 4/1974 | Wagner et al. | 219/521 |
| 3,983,362 | 9/1976 | Hoogesteger et al. | 219/521 |
| 3,983,363 | 9/1976 | Alter | 219/386 |
| 3,998,590 | 12/1976 | Glorieux | 219/439 |
| 4,044,226 | 8/1977 | Kadlecik et al. | 219/521 |
| 4,080,167 | 3/1978 | Beers | 219/385 |
| 4,145,603 | 3/1979 | Mackay et al. | 219/433 |
| 4,165,359 | 8/1979 | Thomas et al. | 219/521 |

FOREIGN PATENT DOCUMENTS

| 2519924 | 11/1976 | Fed. Rep. of Germany | 206/0.8 |
|---|---|---|---|
| 1051578 | 12/1966 | United Kingdom | 219/521 |

Primary Examiner—Thomas J. Kozma
Assistant Examiner—Bernard Roskoski
Attorney, Agent, or Firm—Trexler, Bushnell & Wolters, Ltd.

[57] ABSTRACT

The present invention relates to a thermal disinfecting unit for the disinfecting of a pair of contact lenses disposed within a lens case along with a quantity of disinfecting solution, wherein disinfecting is achieved upon the heating of the solution to a prescribed temperature. The unit as disclosed includes an outer casing made up of upper and lower assembled sections, with an internal heating arrangement disposed therein including a substantially planar lens case support surface. Aperture means are provided in the upper casing section and disposed in relation to the support surface to define a heater well for reception of the lens case. In one embodiment, the aperture means is defined by inwardly extending flange, with a gasket carried thereon, such that as the respective casing sections are drawn together, the gasket will firmly engage the planar support surface to seal the heater well from the interior of the unit. In a second embodiment, a lateral aperture is provided whereby engagement of the lens case with the support surface is attained by a sliding action which serves to wipe the support surface clear of any granular or crystalline substance which may have formed thereon. In addition, the disclosure contemplates an internal heating mechanism designed and constructed, so that the support surface will be heated to a desired temperature and will remain at said temperature for a period of time, before there is any likelihood of operation of a thermostatic device, also carried by said heater block.

24 Claims, 20 Drawing Figures

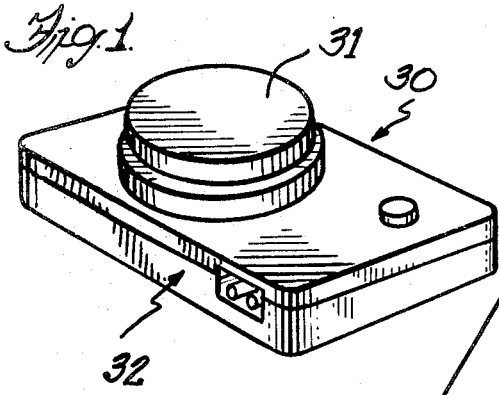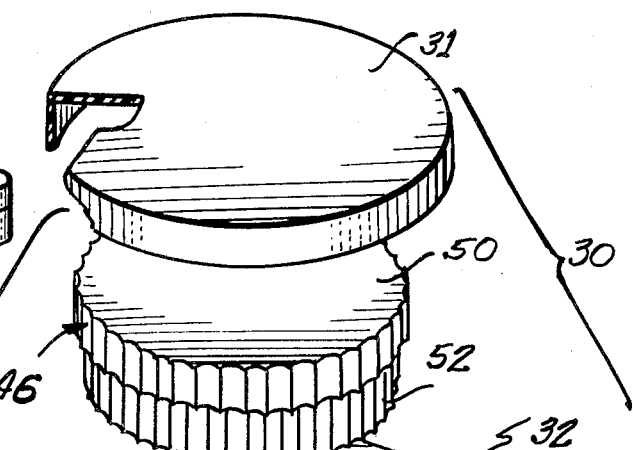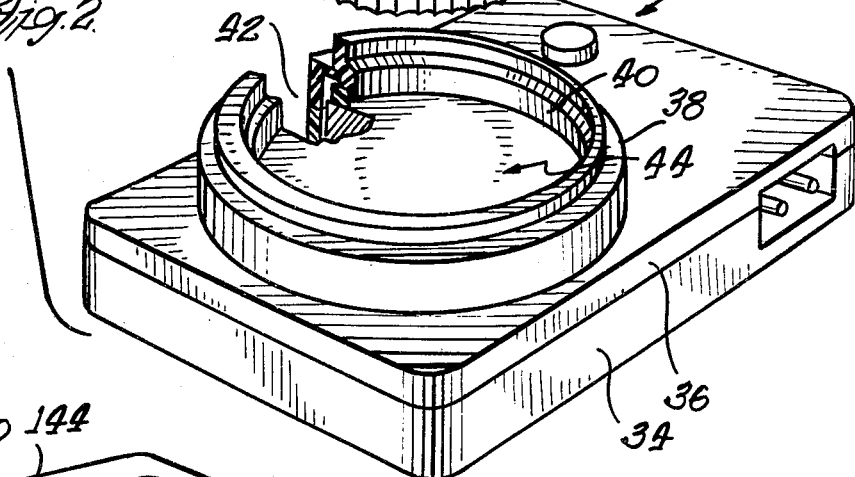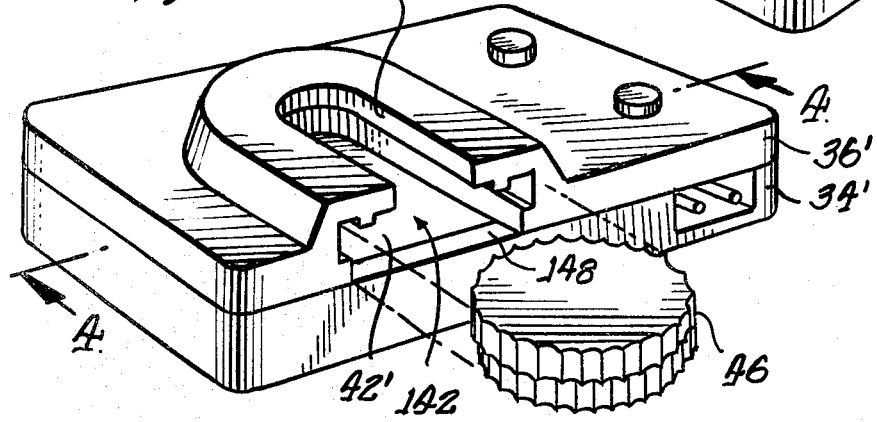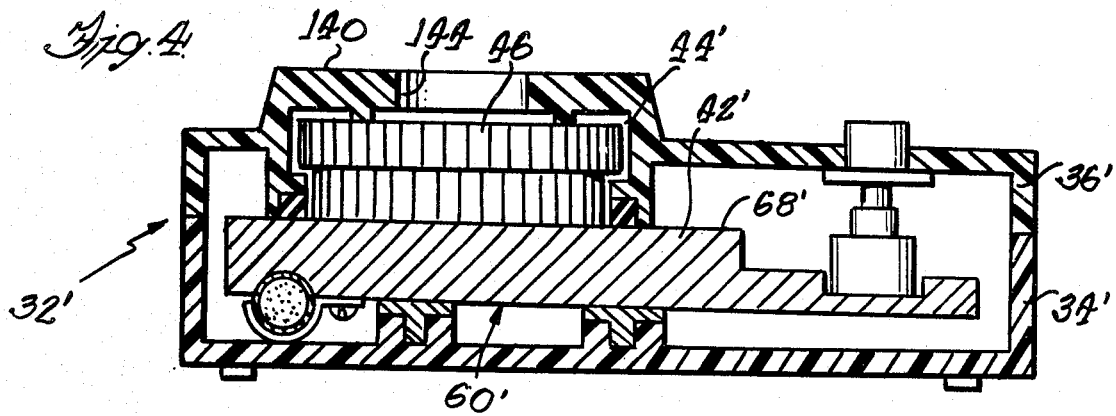

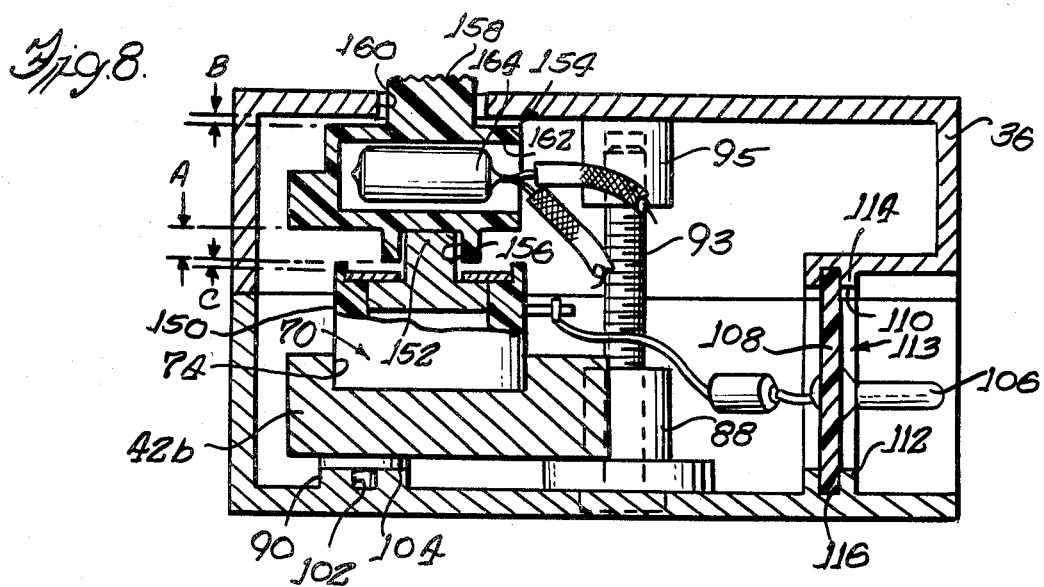
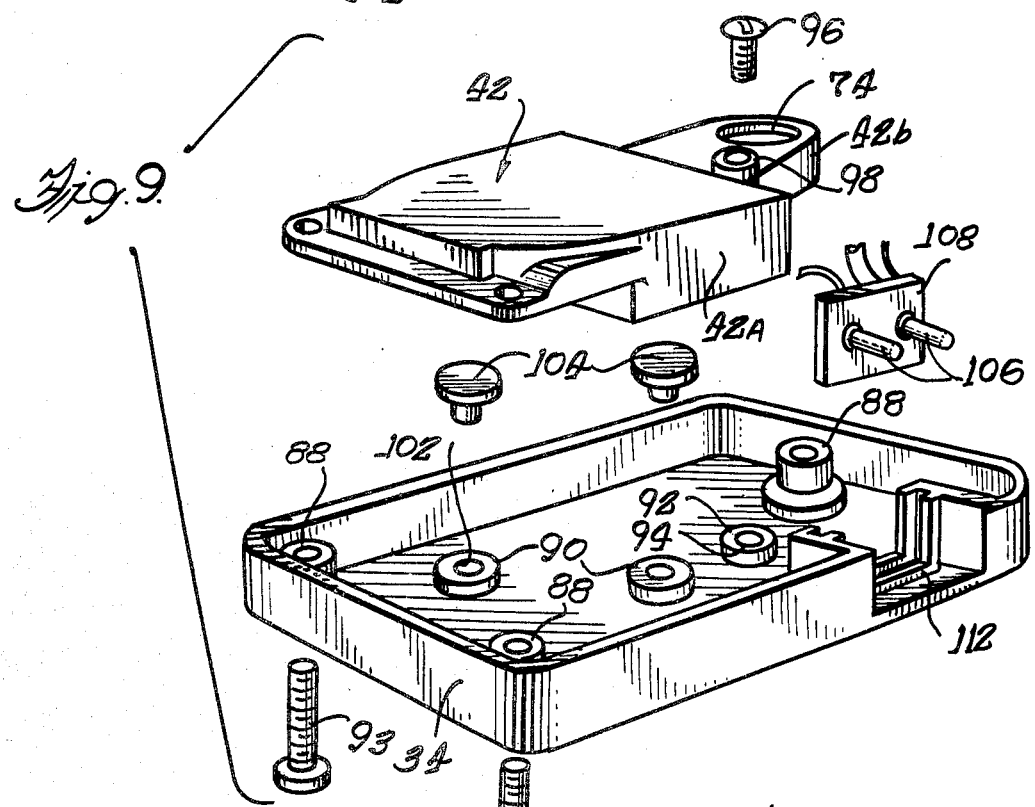
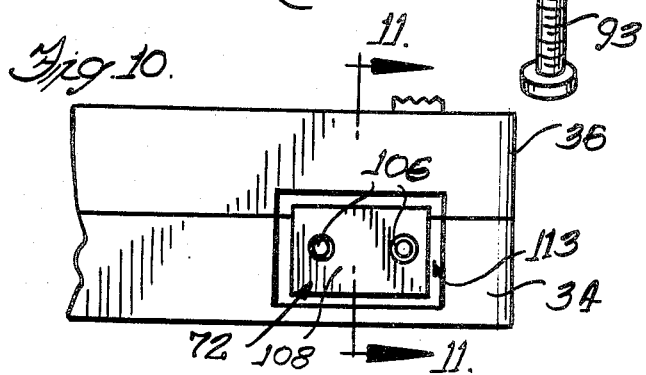
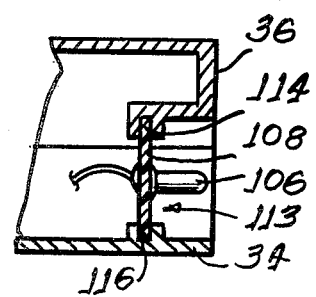

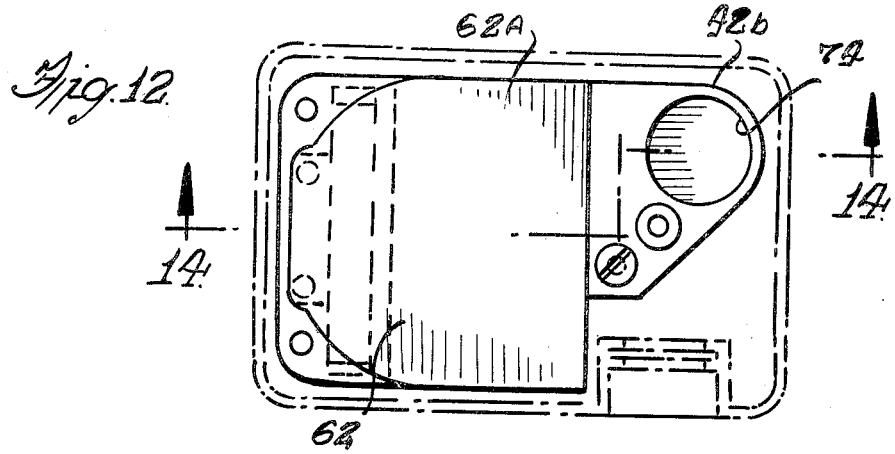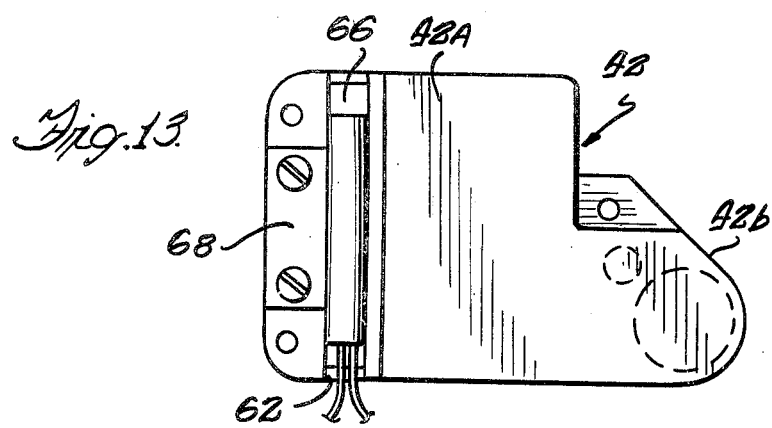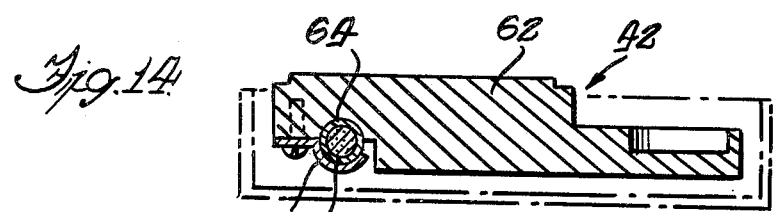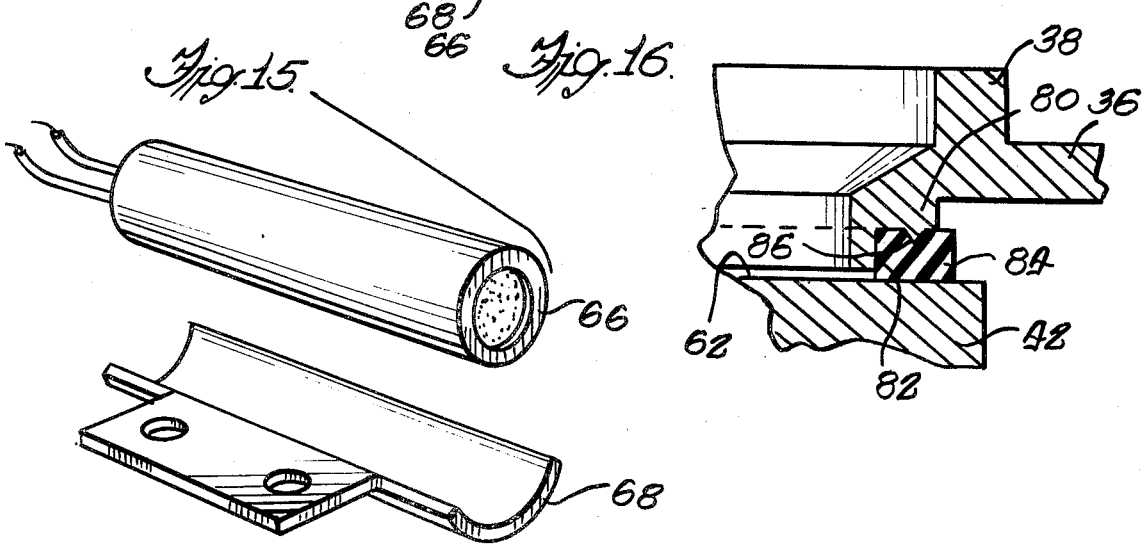

CONTACT LENS DISINFECTING UNIT

BACKGROUND OF THE INVENTION

The present invention pertains to the disinfecting of contact lenses, and more specifically to an improved disinfecting unit for the thermal disinfecting of lenses disposed within a lens case along with a quantity of disinfecting solution, wherein the lens case and the enclosed solution are heated to a specified temperature.

In recent years, soft contact lenses have been developed as an alternative to hard contact lenses, which due to their hardness often irritate the eye, and thus could not be used by many individuals. Soft contact lenses are fabricated from a hydrophilic plastic material, that is a porous plastic material that when dry is firm and can be formed to the desired lens curvature, but will absorb water and become soft and pliable. As can be appreciated, the soft pliable nature of these lenses permit the wearer to adapt more readily to the presence of the lenses on the cornea of the eye.

While hard contact lenses required periodic cleaning and disinfecting, the disinfecting of soft lenses is critical and it is recommended that the lenses be disinfected on a daily basis. The need for frequent disinfecting results due to the porous nature of the plastic material, which provides a medium for bacteria growth that can lead to serious eye infections.

Several disinfecting methods have been developed and employed with success in conjunction with soft lenses. One of the most popular methods involves the disposition of the lenses in a saline or disinfecting solution, and the heating of this solution to a temperature sufficient to destroy any bacteria that might be present. A second method involves the employment of a chemical process to destroy the bacteria. As to the thermal or heat disinfecting methods, this can be accomplished by either "wet heat" process or a more recently developed "dry heat" process; the latter being the process to which the present invention relates. With respect to "wet heat" processes, the lenses are placed in a case which includes a disinfecting solution, and the case is then placed in a second vessel containing a quantity of water which is brought to a boil, with the heat being transferred to the lens case by way of the surrounding water. With a "dry heat" method of sterilization, the lenses are disposed within a lens case and the disinfecting solution added to the case. The case is then placed in surface-to-surface contact with the heater unit, such that direct application of heat is attained from the heater unit to the lens case and the sterilization solution contained therein. Often, the lens case is a sealed vessel which permits heating of the solution above the boiling point, if desired.

The present invention pertains to a disinfecting unit adapted for use in the "dry heat" type of process. In this regard, the present invention has as its main object the provision of an improved disinfecting unit design which is adapted for use with relatively flat lens cases in which the lenses are immersed in a quantity of disinfecting solution. Another object of the present invention is the provision of a novel arrangement for the internal heater mechanism for such a unit, which assures that the support surface and correspondingly the lens case resting thereon are raised to the desired disinfecting temperature, before the heating element is de-energized via a conventional thermostatic device.

The exact manner in which the above-noted objects and other objects of the invention are achieved will become apparent from the following detailed description of the preferred embodiment, taken in conjunction with the accompanying drawings wherein like reference numerals indicate coresponding parts throughout the various views.

DESCRIPTION OF THE DRAWINGS

FIG. 1 is a perspective view of a unit according to the present invention;

FIG. 2 is an exploded perspective view of the unit of FIG. 1 illustrating a typical lens case receivable within the heater well of the unit;

FIG. 3 is a perspective view of an alternate embodiment of the present invention, illustrating the manner in which the lens case is disposed therein;

FIG. 4 is a perspective view through the embodiment of FIG. 3, taken along the line 4—4;

FIG. 8 is an enlarged sectional view taken along the line 8—8 of FIG. 6;

FIG. 9 is an exploded perspective view of the lower casing section, with the heater block element exploded along with elements of the support for said heater block;

FIG. 10 is a partial side elevational view of the terminal arrangement for the disinfecting unit;

FIG. 11 is a partial sectional view taken along the line 11—11 of FIG. 10;

FIG. 12 is a top plan view of the heater block, illustrating in phantom the lower casing section;

FIG. 13 is a bottom plan view of the heater block;

FIG. 14 is a sectional view taken along the broken line 14—14 of FIG. 12;

FIG. 15 is a partial perspective view of the heating element to be employed in conjunction with the heater block along with the thermally conductive clamp therefore;

FIG. 16 is an enlarged perspective view illustrating the engagement of the upper casing structure with the heater block;

DESCRIPTION OF THE ILLUSTRATED EMBODIMENT

Figure 5:
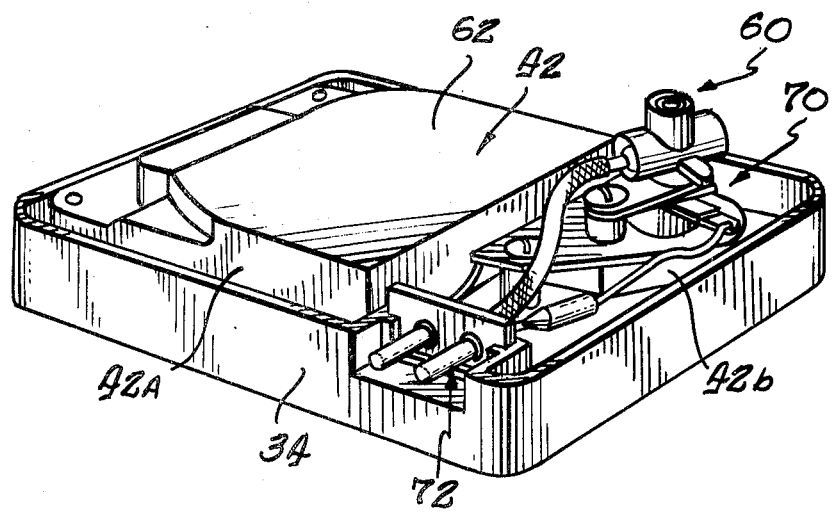
FIG. 5 is a perspective view of the unit of FIG. 2 or 3, with the upper casing section removed, illustrating the internal heating mechanism.
Figure 6:
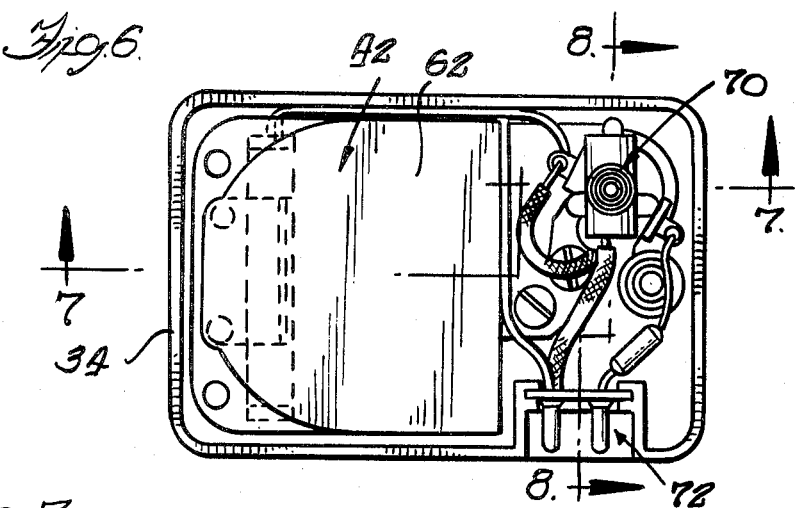
FIG. 6 is a top plan view of the lower casing and internal heating mechanism of FIG. 5.

In FIGS. 1 and 2, there is shown a first form of disinfecting unit in accordance with the present invention, while FIGS. 3 and 4 illustrate a modified form of the invention. More specifically, the embodiment of FIGS. 1 and 2 differs from that of FIGS. 3 and 4 primarily only in the construction of the upper casing section and the manner in which the lens case is received into engagement with the internal heater means. The design or construction of the lower casing section and the internal heater system for the respective embodiments are essentially the same. Accordingly, the remaining figures which relate to said lower casing sections and the internal heating system apply equally to both embodiments. With the above in mind, attention will first be directed to the embodiment of FIGS. 1 and 2 and then to FIGS. 5-20 with respect to the internal construction of the unit, with a description to follow thereafter with respect to the alternate embodiment of FIGS. 3 and 4.

Looking to FIGS. 1 and 2, there is shown a disinfecting unit in accordance with the present invention, which unit is designated generally 30. As can be seen, FIG. 1 illustrates unit 30 in the fully assembled condition with the lens case well cover 31 in place, while FIG. 2 illustrates unit 30 in exploded perspective. The disinfecting unit 30 includes essentially an outer casing or housing 32 comprised of a lower casing section 34, and an upper casing section 36. The internal heater mechanism, to be discussed hereinafter, is disposed within the casing 32. The upper casing element 34 includes an annular raised portion 38 which serves to define an aperture 40. The aperture 40 overlies a support surface of a heater block 42, which forms part of the internal heater mechanism. Said aperture 40 cooperates with said heater block 42 to define a heating well 44 for reception of a lens case 46, which when disposed in said well will be in engagement with the heater block 42. The well cover 31 will overlie the well 40 with the lens case 46 positioned therein.

The specific construction of the lens case 46 is not critical to the present invention, as it may be of a number of known designs, and as such, the internal configuration of the case is not illustrated in detail. The case 46 is however, comprised of releasably engaged upper and lower sections 50 and 52, and provides an internal space for reception of a pair of contact lenses and a quantity of disinfecting solution. Further, the case 46 is preferably of a relatively flat design, including a substantially planar bottom surface which will rest upon the heater block 42 in surface-to-surface, heat conductive engagement.

The internal heater arrangement for the disinfecting unit 30, as mentioned previously, is illustrated in greater detail in FIGS. 5-18, and will now be considered. Looking initially to FIG. 5, this figure is a view of the disinfecting unit 30 with the upper casing section 36 removed, thereby illustrating the lower casing section 34 with the internal heating arrangement 60 mounted therein. It will be recalled, that the heater arrangement 60 and lower casing 34 for both embodiments of the invention are essentially the same, the two embodiments differing with respect to the construction of the upper casing section and the structure provided for accepting the lens case 46.

Returning to the internal heater arrangement 60, it should be noted that said arrangement includes the previously mentioned heater block 42 disposed within the lower casing section 34, which heater block includes an upper, substantially planar support surface 62. As can be seen in FIGS. 13 and 14, the heater block 62 also includes an elongate recess or groove 64 on the undersurface thereof, with a resistance type heater element 66 engaged in said groove, and maintained in heat conductive contact with the block 42 by a heat conductive clamp member 68, FIG. 15.

Electrical power to the resistive heater element 66 is provided by an internal circuit arrangement comprised of a reset type thermostat assembly 70 wired in circuit with the heater 66 and a terminal arrangement 72, both of which will be covered in greater detail hereinafter. The heater element 66 and thermostat 70, and the terminal arrangement 72 function in a conventional manner, in that a cord or conductor (not shown) having a female plug on the end thereof can be affixed to the terminal arrangement 72 to supply current to the heater 66. The thermostat arrangement 70 is of a reset type, and will upon reaching a predetermined temperature, operate automatically to break the circuit to the heater element 66, thereby de-energizing same. When it is desired to again energize the heater 66, the thermostat 70 can be reset to re-establish the circuit, as would occur upon a subsequent heating cycle.

Attention is now directed to the particular design of the heater block 42, as is best shown in FIGS. 9, 12 and 13. In this regard, the heater block 42 is characterized by the inclusion of a relatively massive primary portion 42a, and a less massive, integral extension portion 42b. The primary portion 42a includes the lens case support surface 62 and, on one side thereof, the mounting recess 64 and heating element 66. The extension portion 42b is disposed on the opposite side of the support surface 62 from heater 66 and while formed integral with the primary portion 42a is considerably smaller in width, and also of less mass than said primary portion, for a purpose to be more fully discussed hereinafter. In addition, the extension section 42b includes a recess 74 in which the thermostat assembly 70 may be disposed, see FIG. 7.

The specific construction of the heater block and more importantly, the disposition of the thermostat arrangement 70 on the extension portion 42b, opposite heating element 66 serve a significant function, in that this arrangement assures that the support surface 62 reaches the desired temperature and is maintained at this temperature for a period of time. More specifically, the only source of heat is the heating element 66, and due to its disposition in the recess 64 heat will be applied directly to the heater block 42 and the support surface 62 initially. As to the extension portion 42b, since this portion is of a lesser mass and size than the primary portion 42a, the rate of heat transfer across the juncture of the respective portions 42a and 42b is less than the rate of heat transfer directly from the heater element 66 to the support surface 62. Accordingly, with the thermostatic arrangement 70 disposed in the well 74 on extension 42b, it is assured that by the time the thermostat 70 reaches the "shut off" temperature, i.e. the temperature at which the thermostat operates to break the circuit to the heater 66, the lens support surface 62 will have reached a significantly higher temperature and will have remained at said temperature for a longer period of time. As such, heating of the lens case 46 and the disinfecting solution therein to the necessary temperature required to destroy the bacteria on the lenses can be achieved with a relative degree of assurance that the disinfecting procedure will be completed before the thermostat 70 operates to de-energize the heating element 66.

The design of the casing 32 also provides a number of advantages that cooperate to provide an improved disinfecting unit design. Initially, attention is directed to FIGS. 7 and 16, and the construction of the upper casing section 36. As can be seen, casing section 36 includes a downwardly, inwardly depending annular flange portion 80 which is in effect an inward extension of the raised portion 38, and serves to define partially the aperture 40 in the casing section, and correspondingly part of the heating well 44. As is shown on an enlarged scale in FIG. 16, the flange portion 80 includes an annular inwardly opening groove 82, with a gasket 84 disposed in said groove and extending axially past the end of flange 80. Upon assembly of the respective casing sections 34 and 36 with the use of a screw fastener, as will be discussed with regard to FIG. 9, the respective sections 34 and 36 will be drawn together, bringing the gasket 84 into firm sealed contact with the support surface 62. Further, if desired, the casing 36 may include an annular projection 86 to engage the gasket and intensify the sealing force. In either instance, the gasket arrangement 84 serves to effectively seal the well 44 from the interior of the casing 32, which is an important feature since there is always the danger that the liquid disinfecting solution may spill into the well 44, and leak to the interior of the casing, resulting in the possibility that a short circuit or electrical shock may occur. With the arrangement as illustrated, the well 44 is effectively sealed with respect to the interior of the casing 32, and no danger of leakage and shock exists.

Figure 7:
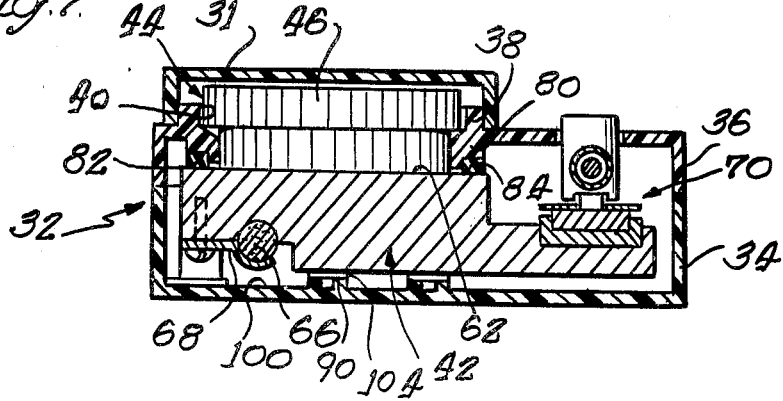
FIG. 7 is a sectional view taken along the line 7—7 of FIG. 6, but illustrating the entire mechanism with the lens case in place.

A second feature of the casing section 32 is the provision of an insulating arrangement which serves to isolate the heater block 42 from the bottom wall of the lower casing section 34, thereby precluding said lower casing bottom wall from becoming excessively hot, and damaging the underlying surface upon which the unit 30 may be resting. In this regard, attention is invited to FIGS. 7-9 and primarily FIG. 9 where it can be seen at the lower casing section 34 includes a plurality of integral, upstanding posts or support members, a first set of which is designated 88, a second set 90, and an intermediate member 92. The post members 88 are provided with through apertures, and are designed to receive fastener members 93 which are engaged in corresponding apertured post means 95 (FIG. 8), provided in the upper casing section 36, wherein said fasteners 93 serve to draw the sections 34 and 36 together and maintain the casing 32 in assembled relation. As to the intermediate post element 92, this element is provided with an internally threaded bore 94 adapted to receive the fastener 96, which is engageable in an aperture 98 formed in the heater block, with the fastener 96 serving to affix the heater block 42 to the lower casing section 34. The second set of supports or posts 90 are each raised above the bottom wall 100 of the casing section 34 and each is provided with a blind aperture 102. A pair of studs 104 are provided, which studs are formed from a heat insulating material and as can be seen in FIGS. 7 and 8 said studs are mounted in the blind apertures 102 of posts 90. Accordingly, in the assembled condition, FIG. 7, the heater block 42 will rest upon the insulating studs 104, and said heater block will be spaced above the bottom wall 100 of the casing. Thus, the studs 104 retard the rate of heat transfer from the heater block 42 to the casing via the post 90, and the air space between the bottom wall 100 and the heater block 42 provides an air insulation barrier that prevents the casing bottom 100 from becoming excessively hot, which could result in damage to an underlying support surface.

A third feature of the casing 32 is the manner in which the terminal arrangement 72 is provided, which arrangement is illustrated in numerous figures of the drawings, and will be discussed primarily with respect to FIGS. 8 and 9. The terminal arrangement 72 includes a pair of male terminal pins 106 mounted to a phenolic board or plate-like member 108 which provides an insulator between the respective terminal pins. Terminal pins 106 as shown in various figures are wired in circuit with the thermostat arrangement 70 and the heater element 66, and are of a conventional design adapted to be engaged with a complementary female connector (not shown) mounted on a conductor leading to a power source. Both the upper and lower casing sections 34 and 36 are provided with partial complementary openings or cutouts designated 110 and 112, respectively, which are recessed from the edge of the casing 32, and when the casing sections 34 and 36 are assembled, cooperate to define an aperture 113. The openings in the respective casing sections 34 and 36 are provided by a pair of spaced flanges which serve to define grooved portions 114 and 116, extending about the periphery of the aperture 113. The groove portions 114 and 116 are sized to receive the edges of the phenolic board 108, such that upon assembly, as shown in FIG. 8, and also FIGS. 10 and 11, the board is disposed within said grooves 114 and 116, and serves to close the aperture 113, and preclude access to the interior of the casing and the internal circuit means therein.

Figure 17:
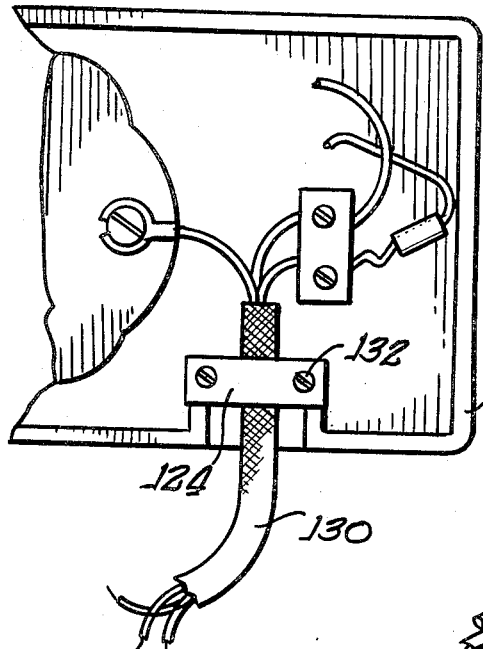
FIG. 17 is a partial top plan view of an alternative arrangement for the disinfecting unit.
Figure 18:
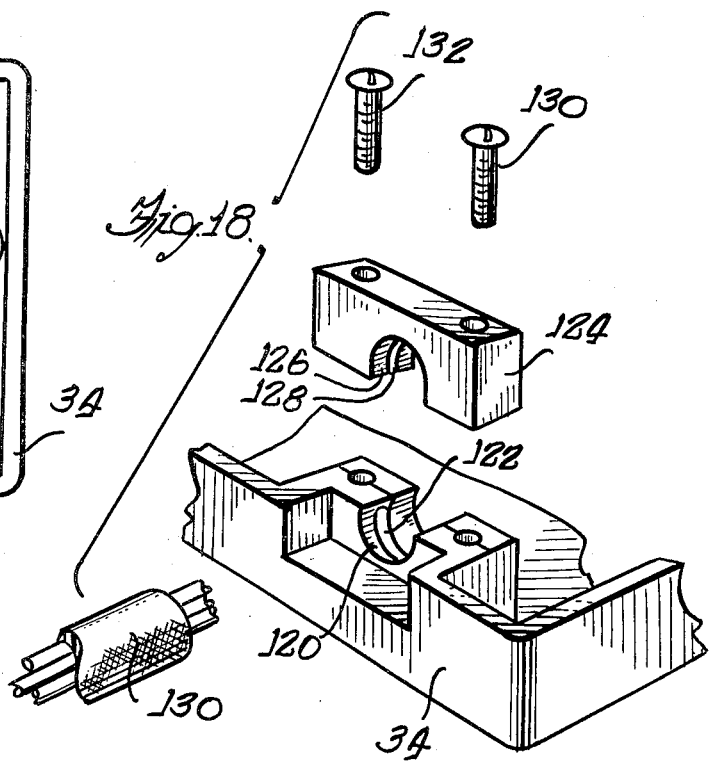
FIG. 18 is an exploded perspective view of the terminal arrangement as illustrated in FIG. 17.

An alternate form of terminal means to the terminal arrangement 72 as discussed above is illustrated in FIGS. 17 and 18, wherein a three-wire type of conductor is shown. In this regard, the lower casing section 34 is provided with an opening 120 which is of a generally semi-circular nature and includes a rib 122 on the interior surface thereof. A clamping block 124 is provided which includes a semi-circular opening 126, complementary to the previously mentioned opening 120 and also includes a rib 128 on the interior surface thereof. Upon assembly, as shown in FIG. 17, the three-wire connector 130 is disposed in the semi-circular opening or groove 120, and is clamped in place via the clamping block 124 by use of the screws 132, as shown. The complementary ribs 122 and 128 serve firmly to grip the three-wire conductor 130, and provide a measure of strain relief; that is should an axially directed strain be placed upon the wire 130, said strain will be taken up by the ribs 122 and 128 which are engaged with the outer wire casing rather than said strain being transmitted to the internal connection of the individual wires of the conductor element.

Figure 19:
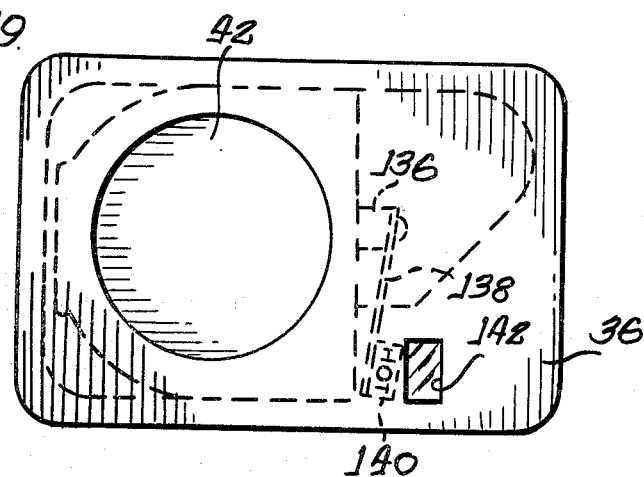
FIGS. 19 and 20 illustrate schematically a temperature status indicator that may be employed with the disinfecting unit embodiments of FIGS. 2 or 3.
Figure 20:
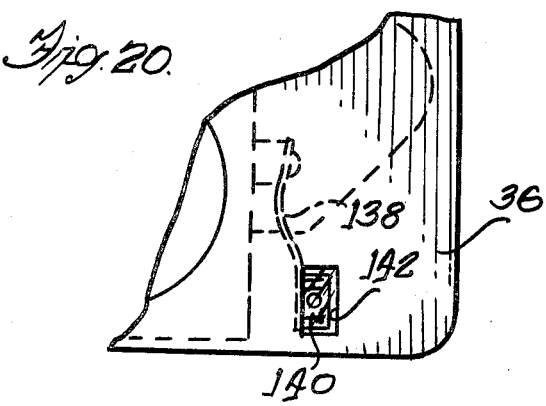

In FIGS. 19 and 20, there is illustrated an optional feature that may be employed with the disinfecting units of the present invention, said feature providing the indication as to the status or condition of the heat support surface. More specifically, a stud or block 136 is formed integral with the heater block 42, and a bi-metallic strip 138 is affixed thereto. On the remote or distal end of the bi-metallic strip 138 there is provided an indicia carrying placard 140 which carries the word "HOT" or some commonly recognized indication of elevated temperature, such as the color red. The upper casing member 36 is provided with a viewing window 142 and the bi-metallic strip is arranged, such that in the normal or ambient state, viz. preheat the placard 140 will be offset with respect to the viewing window 142. Accordingly, as the temperature of the heater block 42 is elevated, the bi-metallic strip 138 will flex to the right as viewed, and as illustrated in FIG. 20, this movement brings the indicia carrying placard 140 beneath the viewing window 142, thus providing a visual indication to the user that the disinfecting unit is at an elevated temperature.

Attention is now invited back to FIGS. 3 and 4, wherein a second embodiment of the heater unit invention is shown, this unit being designated 30'. As mentioned above, the construction of the lower casing 34' and the internal heater system 60' of the unit 30' is essentially the same as discussed relative to the unit 30. As such, a detailed description of these features is not deemed necessary. The upper casing section 36' and the manner of accepting the lens case 46, however, are different in this embodiment and will be discussed.

Looking first to FIG. 3, the upper casing section 36' includes a raised portion 140 in which there is provided a lateral aperture 142, with the upper surface of the raised portion 140 also including a slot 144 extending through to aperture 142. The aperture 142 is disposed relative to the heater block 42' to define a heater well 44' for reception of the lens case 46, with said case 46 disposed in surface-to-surface contact with the support surface 68' of the heater block. As an additional matter, the support surface 68' is disposed flush with respect to the upper edge 148 of casing section 34 and in abutment with the side wall of said casing section, as shown in FIG. 3. The aforementioned slot 144 serves to facilitate removal of the lens case 46 upon completion of the disinfecting cycle, as it permits the user to grasp the lens case and slide it out of the casing well.

As can be appreciated from a viewing of FIGS. 3 and 4, the movement of the lens case 46 upon disposition in the well 44' and removal, is a lateral, sliding action with respect to the support surface 68'. This movement serves as a wiping action to maintain the surface 68' free of any granular or crystalline particles. More specifically, the disinfecting solutions utilized are primarily of a saline type, and if any is spilled on the surface 68', the heat generated will evaporate the water, leaving salt crystals. These crystals, upon subsequent disinfecting procedures will prevent the desired surface-to-surface contact of the lens case with the heater block support surface, a feature important in attaining the most efficient heat transfer to the case 46.

An additional feature of the invention that can be used with either embodiment is the specific design of the thermostat assembly 70, which facilitates and simplifies assembly. With reference to FIG. 8, the thermostat assembly 70 includes a thermostat device 150 in circuit with the terminal pins 106 and the resistive heating element 66 (not shown in FIG. 8); a reset plunger 152; and an actuator button 154. The actuator button 154 includes a recess 156 in which the reset plunger 152 is disposed, and a projection 158 which extends through an opening 160 in the upper casing 36. In addition, there is provided a transverse recess 162, in which a light bulb 164 is disposed for a purpose to be discussed.

The thermostat 150 with its reset plunger 152 is of the reset type and of generally conventional design. In this regard, the thermostat 150 includes a bi-metallic member, (not shown) such that when a preset temperature is reached the reset plunger 152 is raised and the circuit broken. When it is desired again to energize the heater, the reset plunger 152 is depressed to re-establish the circuit to the heater element. As can be appreciated from FIG. 8, the thermostat reset plunger 152 may be operated by manipulation of the actuator button 158 from the exterior of the unit.

The design and construction of the actuator button 158 is such that in the fully completed condition for the unit, button 158 is maintained in captive assembly, and this relationship is attained without use of any fastener or the like, relying solely upon the dimensioned features of the various components. More specifically, the maximum stroke of degree of movement of the actuator button 158 with respect to the reset plunger 152 can occur when said plunger is depressed and the button 158 engages the thermostat 70. In FIG. 8, the reset plunger 152 is extended and this extent of movement is represented by the dimensions "B" and "C". The recess 156 is dimensioned such that the depth "A" thereof is greater than "B" plus "C". As such, the recess 156 and the extension 158 protruding from the casing aperture 160 precludes movement of the actuator button 158 from the assembled condition, thereby maintaining a captive assembly.

The lamp 164 is wired in circuit with the heater 64, and as such will only be energized when power is supplied to the heater. Disposition of the lamp 164 in recess 162 will cause the actuator button 154 to glow providing a visual indication that the heater is energized.

A preferred embodiment of the present invention has been illustrated and described above. While the specific structural features discussed constitute preferred forms, they are not intended to limit the invention, as it is contemplated that those skilled in the art and possessed with the form of the invention illustrated may devise alternate structures without departing from the spirit and scope of the invention, as defined in the claims appended hereto.

The invention is claimed as follows:

1. A contact lens disinfecting unit for the thermal disinfecting of a pair of contact lenses or the like disposed within a lens case and immersed in a disinfecting solution contained within the case, said disinfecting unit comprising an outer casing including upper and lower casing sections, and heater means disposed internally of said casing, which heater means includes a heater block having a substantially planar support surface, and circuit means for effecting controlled resistive heating of said heater block, said circuit means includes a resistive type heating element, and a thermostat device in circuit with said heating element for de-energizing said heating element when said thermostat reaches the preset temperature and said thermostat device being manually resetable to energize said heating element, and said heater block including a primary segment having said support surface thereon, with a recess formed in said primary segment with said resistive heating element received in said recess in heat conductive engagement therewith for transmitting heat to a lens case resting on said support surface, and said heater block further including an extension segment, integral with and extending from said primary segment and having said thermostat device disposed thereon, said extension segment being disposed on the side of said support surface opposite said heating element, and being of substantially less size and mass than said primary segment, such that the rate of heat transfer to said thermostat device through said heater block wil be less than the rate of heat transfer to said support surfaces, thereby assuring that said support surface reaches a desired temperature and remains at that temperature for a period of time, before said thermostat device is actuated to de-energize said heating element, said upper casing section having aperture means including an inwardly extending flange portion, which aperture means overlies said planar support surface and defines therewith a heating well adapted to receive a lens case therein, with said lens case disposed in heat conductive engagement with said heater block support surface, said inwardly extending flange portion including a peripheral groove, and a gasket member disposed in said groove and extending axially beyond said flange portion in facing relation to said planar support surface, and means for assembling said upper and lower casing sections, which draw said sections together bringing said gasket into compressed engagement with said planar support surface, thereby effectively sealing said lens case well from the interior of said casing and preventing the entry of any liquid to the interior of said casing which could adversely effect said circuit means.

2. A disinfecting unit according to claim 1, wherein said lower casing section includes a bottom wall and a plurality of support members formed integral with said bottom wall and extending upwardly therefrom, with said heater block resting upon said support members and disposed in spaced relation with respect to said bottom wall, thereby providing an air insulation barrier between said heater block and said bottom wall.

3. A contact lens disinfecting unit according to claim 1, wherein said circuit means includes a terminal arrangement comprised of a non-conductive plate member, with male terminal elements carried by said plate member and extending from said plate member exteriorly of said casing for connection with a conductor having a cooperating female type connector thereon, said terminal arrangement comprising partial, complementary aperture means formed in both said upper and lower casing sections, each said aperture means including inwardly facing slot means, such that when said casing sections are assembled, there is provided an aperture therein surrounded by said slot means, and said plate member being received in said slot means to close said aperture, and thereby prevent access to the interior of said casing through said aperture.

4. A contact lens disinfecting unit according to claim 1, wherein said extension segment includes a well, with said thermostat device disposed in said well.

5. A contact lens disinfecting unit according to claim 1, wherein said circuit means includes a resistive heating element and control means for said heating element in the form of a thermostatic device disposed internally of said casing, which thermostatic device includes a reset plunger, an actuator button engaged with said reset plunger and in the assembled condition being disposed between said plunger and the upper casing section, with a segment of said actuator button extending exteriorly of the casing through an aperture formed in said casing, for manual engagement of said actuator button to operate said reset plunger, said actuator button including a recess, in which said reset plunger is received, the depth of said recess being greater than the extent of maximum movement permitted said actuator button such that the engagement of said reset plunger in said recess and the extension of said actuator button segment through the casing aperture, serve to maintain said actuator button in captive assembly with respect to said thermostatic device and said casing.

6. A contact lens disinfecting unit according to claim 5, wherein said actuator button includes a transverse, intermediate recess, a light source disposed in said intermediate recess, which source is wired in circuit between said thermostat and said heater element, such that said light source will be energized and said actuator button will be illuminated when said heater unit is energized.

7. In combination, a relatively flat lens case and a contact lens disinfecting unit for the thermal disinfecting of contact lenses disposed within said lens case along with a quantity of disinfecting solution, said disinfecting unit comprising; a casing having an upper surface; heater means disposed internally of said casing and including a thermally conductive support surface for the lens case; a lateral opening formed in said casing of a size to permit the lens case to be inserted therethrough and disposed for engagement on said support surface, the lower periphery of said lateral opening being disposed substantially at or below the level of said support surface, such that primarily relative level movement is employed upon disposition or removal of the lens case to or from a position wherein said lens case is supported on said support surface, said resulting relative lateral movement causing the bottom of said lens case to slide over said support surface with a wiping action which serves to remove any granular or crystalline material which may have formed on said support surface and which might prevent flush surface-to-surface heat conductive contact between said lens case and said support surface, and slot means formed in said casing to facilitate removal of the lens case once the thermal disinfecting operation is completed.

8. The combination according to claim 7 wherein said slot means is formed in the upper surface of said casing and communicates with said lateral opening.

9. A contact lens disinfecting unit for the thermal disinfecting of contact lenses disposed within a relatively flat lens case, along with a quantity of disinfecting solution, said disinfecting unit comprising: a casing; heater means disposed internally of said casing and including a thermally conductive support surface for a lens case, said heater means further including a resistive type heating element, and a thermostat device in circuit with said heating element for de-energizing said heating element when said thermostat reaches the preset temperature and said thermostat device being manually resetable to energize said heating element, and a heater block including a primary segment having said support surface thereon, with a recess formed in said primary segment with said resistive heating element received in said recess in heat conductive engagement therewith for transmitting heat to a lens case resting on said support surface, and said heater block further including an extension segment, integral with and extending from said primary segment and having said thermostat device disposed thereon, said extension segment being disposed on the side of said support surface opposite said heating element, and being of substantially less size and mass than said primary segment, such that the rate of heat transfer to said thermostat device through said heater block will be less than the rate of heat transfer to said support surfaces, thereby assuring that said support surface reaches a desired temperature and remains at that temperature for a period of time, before said thermostat device is actuated to de-energize said heating element a lateral opening formed in said casing of a size to permit a lens case to be disposed therein by movement laterally of said support surface, said lateral opening and said lens case support surface being disposed such that upon disposition or removal of a lens case the resulting relative lateral movement will cause the bottom of said case to slide over said support surface with a wiping action which serves to remove any granular or crystalline material which may have formed on said support surface and which might prevent flush surface-to-surface heat conductive contact between said lens case and support surface.

10. A contact lens disinfecting unit for the thermal disinfecting of a pair of contact lenses disposed within a lens case and immersed in a disinfecting solution contained within the case, said disinfecting unit comprising, a casing structure, and heater means disposed internally of said casing, which heater means includes a heater block providing a substantially planar support surface, and circuit means for effecting controlled resistive heating of said heater block, said casing structure including aperture means adapted to receive a lens case therein, with said lens case disposed in heat conductive engagement with said heater block support surface, said circuit means including a resistive type heating element, and a thermostat device in circuit with said heating element for de-energizing said heating element when said thermostat reaches the preset temperature and said thermostat device being manually resetable to energize said heating element, and said heater block including a primary segment having said support surface thereon, with a recess formed in said primary segment with said resistive heating element received in said recess in heat conductive engagement therewith for transmitting heat to a lens case resting on said support surface, and said heater block further including an extension segment, integral with and extending from said primary segment and having said thermostat device disposed thereon, said extension segment being disposed on the side of said support surface opposite said heating element, and being of substantially less size and mass than said primary segment, such that the rate of heat transfer to said thermostat device through said heater block will be less than the rate of heat transfer to said support surfaces, thereby assuring that said support surface reaches a desired temperature and remains at that temperature for a period of time, before said thermostat device is actuated to de-energize said heating element.

11. A contact lens disinfecting unit according to claim 10, wherein said extension segment includes a well, with said thermostat device disposed in said well.

12. A contact lens disinfecting unit according to claim 10, wherein said thermostatic device inlcudes a reset plunger, an actuator button engaged with said reset plunger and in the assembled condition being disposed between said plunger and the upper casing section, with a segment of said actuator button extending exteriorly of the casing through an aperture formed in said casing, for manual engagement of said actuator button to operate said reset plunger, said actuator button including a recess, in which said reset plunger is received, the depth of said recess being greater than the extent of maximum movement permitted said actuator button such that the engagement of said reset button segment through the casing aperture, serve to maintain said actuator button in captive assembly with respect to said thermostatic device and said casing.

13. A contact lens disinfecting unit according to claim 12, wherein said actuator button includes a transverse, intermediate recess, a light source disposed in said intermediate recess, which source is wired in circuit between said thermostat and said heater element, such that said light source will be energized and said actuator button will be illuminated when said heater unit is energized.

14. A contact lens disinfecting unit according to claim 10, wherein said aperture means includes a lateral opening formed in said casing of a size to permit a lens case to be disposed therein by movement laterally of said support surface, said lateral opening and said lens case support surface being disposed such that upon disposition or removal of a lens case the resulting relative lateral movement will cause the bottom of said case to slide over said support surface with a wiping action which serves to remove any granular or crystalline material which may have formed on said support surface and which might prevent flush surface-to-surface heat conductive contact between said lens case and said support surface.

15. A disinfecting unit according to claim 14 wherein said casing includes slot means formed in the upper surface thereof and communicating with said lateral opening to facilitate the removal of a lens case once the thermal disinfecting operation is completed.

16. A contact lens disinfecting unit according to claim 10 wherein said aperture means overlies said planar support surface and defines therewith a heating well for receiving said lens case, and said aperture means is defined partially by an inwardly extending flange portion including a peripheral groove, a gasket member disposed in said groove and extending axially beyond said flange portion in facing relation to said planar support surface, and means for assembling said casing to bring said gasket into compressed engagement with said planar support surface thereby effectively sealing the interior of said casing from said well and preventing the entry of any liquid to the interior of said casing which would adversely effect said circuit means.

17. A contact lens disinfecting unit for the thermal disinfecting of a pair of contact lenses or the like disposed within a lens case and immersed in a disinfecting solution contained within the case, said disinfecting unit comprising: a casing structure including upper and lower casing sections, and heater means disposed internally of said casing, said circuit means for effecting control of the operation of said heater means, said circuit means including a resistive type heating element, and a thermostat device in circuit with said heating element for de-energizing said heating element when said thermostat device reaches the preset temperature and said thermostat device being manually resetable to energize said heating element, and said heater block including a primary segment having said support surface thereon, with a recess formed in said primary segment with said resistive heating element received in said recess in heat conductive engagement therewith for transmitting heat to a lens case resting on said support surface, and said heater block further including an extension segment, integral with and extending from said primary segment and having said thermostat device disposed thereon, said extension segment being disposed on the said of said support surface opposite said heating element, and being of substantially less size and mass than said primary segment, such that the rate of heat transfer to said thermostat device through said heater block will be less than the rate of heat transfer to said support surfaces, thereby assuring that said support surface reaches a desired temperature and remains at that temperature for a period of time, before said thermostat device is actuated to de-energize said heating element, said circuit means further including a terminal arrangement comprised of a non-conductive plate member with male terminal elements carried by said plate member and extending from said plate member exteriorly of said casing for connection with a conductor having a cooperating female type connector thereon, said terminal arrangement further comprising partial, complementary aperture means formed in both said upper and lower casing sections, each said aperture means including inwardly facing slot means, such that when said casing sections are assembled, there is provided a complete aperture therein surrounded by said slot means, and said plate member being received in said slot means to close said aperture, and thereby prevent access to the interior of said casing through said aperture.

18. A disinfecting unit according to claim 17, wherein said lower casing section includes a bottom wall and a plurality of support members formed integral with said bottom wall and extending upwardly therefrom, and said heater means includes a heater block resting upon said support members and disposed in spaced relation with respect to said bottom wall, thereby providing an air insulation barrier between said heater block and said bottom wall.

19. A contact lens disinfecting unit according to claim 18, wherein said extension segment includes a well, with said thermostat device disposed in said well.

20. A contact lens disinfecting unit according to claim 17, wherein said upper casing section having aperture means including an inwardly extending flange portion, which aperture means overlies a planar support surface of the heater means and defines therewith a heating well adapted to receive a lens case therein, with said lens case disposed in heat conductive engagement with said support surface, said inwardly extending flange portion including a peripheral groove, and a gasket member disposed in said groove and extending axially beyond said flange portion in facing relation to said planar support surface, and means for assembling said upper and lower casing sections, which draw said sections together bringing said gasket into compressed engagement with said planar support surface, thereby effectively sealing the well from the interior of said casing.

21. A contact lens disinfecting unit according to claim 17, wherein there is provided aperture means in said upper casing, for receipt of a lens case, said aperture means including a lateral opening formed in said casing of a size to permit a lens case to be disposed therein by movement laterally of a support surface provided by said heater means, said lateral opening and said support surface being disposed such that upon disposition or removal of a lens case the resulting relative lateral movement will cause the bottom of said case to slide over said support surface with a wiping action which serves to remove any granular or crystalline material which may have formed on said support surface and which might prevent flush surface-to-surface heat conductive contact between said lens case and said support surface.

22. A disinfecting unit according to claim 21, wherein said casing includes slot means formed in the upper surface thereof and communicating with said lateral opening to facilitate the removal of a lens case once the thermal disinfecting operation is completed.

23. A contact lens disinfecting unit for the thermal disinfecting of a pair of contact lenses or the like disposed within a lens case and immersed in a disinfecting solution contained within the case, said disinfecting unit comprising an outer casing including upper and lower casing sections, and heater means disposed internally of said casing, which heater means includes a heater block having means for accommodating a lens case in heat conductive association therewith, and circuit means for effecting resistive heating of said heater block, said circuit means including a resistive type heating element, and a thermostat device in circuit with said heating element for de-energizing said heating element when said thermostat reaches the preset temperature and said thermostat device being manually resetable to energize said heating element, and said heater block including a primary segment having said support surface thereon, with a recess formed in said primary segment with said resistive heating element received in said recess in heat conductive engagement therewith for transmitting heat to a lens case resting on said support surface, and said heater block further including an extension segment, integral with and extending from said primary segment and having said thermostat device disposed thereon, said extension segment being disposed on the side of said support surface opposite said heating element, and being of substantially less size and mass than said primary segment, such that the rate of heat transfer to said thermostat device through said heater block will be less than the rate of heat transfer to said support surfaces, thereby assuring that said support surface reaches a desired temperature and remains at that temperature for a period of time, before said thermostat device is actuated to de-energize said heating element, said lower casing section including a bottom wall and a plurality of support members formed integral with said bottom wall and extending upwardly therefrom, with said heater block resting upon said support members and disposed in spaced relation with respect to said bottom wall, thereby providing an air insulation barrier between said heater block and said bottom wall.

24. A contact lens disinfecting unit according to claim 23, wherein said extension segment includes a well, with said thermostat device disposed in said well.

* * * * *

UNITED STATES PATENT AND TRADEMARK OFFICE
CERTIFICATE OF CORRECTION

PATENT NO. : 4,307,289

DATED : December 22, 1981

INVENTOR(S) : MICHAEL D. THOMAS & FRANCIS E. RYDER

It is certified that error appears in the above-identified patent and that said Letters Patent are hereby corrected as shown below:

Column 10, line 7, change "level" to --lateral--;

Column 12, line 30, after the comma, change "said" to --and--;

Column 12, line 47, change "said", first occurrence, to --side--.

Signed and Sealed this

Sixth Day of April 1982

[SEAL]

Attest:

GERALD J. MOSSINGHOFF

Attesting Officer    Commissioner of Patents and Trademarks